United States Patent
Bader

(10) Patent No.: US 11,453,414 B2
(45) Date of Patent: Sep. 27, 2022

(54) METHOD AND DEVICE FOR ADAPTING A DRIVING STRATEGY OF AN AT LEAST PARTIALLY AUTOMATED TRANSPORTATION VEHICLE

(71) Applicant: VOLKSWAGEN AKTIENGESELLSCHAFT, Wolfsburg (DE)

(72) Inventor: Viktor Bader, Wolfsburg (DE)

(73) Assignee: Volkswagen Aktiengesellschaft

( * ) Notice: Subject to any disclaimer, the term of this patent is extended or adjusted under 35 U.S.C. 154(b) by 243 days.

(21) Appl. No.: 16/830,699

(22) Filed: Mar. 26, 2020

(65) Prior Publication Data

US 2020/0307647 A1  Oct. 1, 2020

(30) Foreign Application Priority Data

Mar. 27, 2019 (DE) ...................... 10 2019 204 201.5

(51) Int. Cl.
*B60W 60/00* (2020.01)
*A61B 5/00* (2006.01)
(Continued)

(52) U.S. Cl.
CPC ..... *B60W 60/00133* (2020.02); *A61B 5/4809* (2013.01); *A61B 5/4812* (2013.01);
(Continued)

(58) Field of Classification Search
CPC ....... B60W 60/00133; B60W 60/0016; B60W 2040/0827; B60W 2540/229; B60W 2720/106; A61B 5/4809; A61B 5/812; A61B 5/6893; A61B 2503/12; G01C 21/3461; G01C 21/3484
See application file for complete search history.

(56) References Cited

U.S. PATENT DOCUMENTS 9,500,489 B1 * 11/2016 Ng ...................... G01C 21/3484
10,004,873 B1 * 6/2018 Hur ...................... G05D 1/0274
(Continued)

FOREIGN PATENT DOCUMENTS

CA        3069357 A1    1/2019
DE   102013012750 A1    2/2015
(Continued)

*Primary Examiner* — Dale W Hilgendorf
(74) *Attorney, Agent, or Firm* — Barnes & Thornburg, LLP

(57) ABSTRACT

A method for adapting a driving strategy of a transportation vehicle driving in at least semi-automated state, wherein the adapting takes place based on at least one occupant condition, captured by at least one sensor system, of an occupant, wherein a sleep phase is determined by the at least one sensor system during a sleeping condition of the occupant, wherein the driving strategy is adapted by a control device based on the determined sleep phase. An apparatus for adapting a driving strategy of a transportation vehicle driving in at least semi-automated state having at least one sensor system for capturing an occupant condition of an occupant, and a control device for adapting the driving strategy, wherein the at least one sensor system determines a sleep phase during a sleeping condition of the occupant, and wherein the control device adapts a driving strategy based on the determined sleep phase.

17 Claims, 3 Drawing Sheets

(51) Int. Cl.
  *G01C 21/34*  (2006.01)
  *B60W 40/08*  (2012.01)

(52) U.S. Cl.
  CPC ........... *A61B 5/6893* (2013.01); *B60W 40/08* (2013.01); *G01C 21/3461* (2013.01); *A61B 2503/12* (2013.01); *B60W 2040/0827* (2013.01); *B60W 2540/221* (2020.02); *B60W 2540/229* (2020.02); *B60W 2720/106* (2013.01); *G01C 21/3484* (2013.01)

(56) References Cited

U.S. PATENT DOCUMENTS

| | | | | |
|---|---|---|---|---|
| 10,235,859 | B1 * | 3/2019 | Hiles | B60W 40/09 |
| 10,272,920 | B2 * | 4/2019 | Shikii | B60W 50/14 |
| 2007/0080816 | A1 * | 4/2007 | Haque | B60W 50/14 |
| | | | | 340/576 |
| 2016/0357185 | A1 * | 12/2016 | Laur | B60W 50/0098 |
| 2016/0377447 | A1 * | 12/2016 | DeLuca | G06N 5/00 |
| | | | | 701/400 |
| 2018/0319279 | A1 * | 11/2018 | Ikeda | B60W 50/16 |
| 2018/0335776 | A1 | 11/2018 | Theis et al. | |
| 2019/0231256 | A1 * | 8/2019 | Jantunen | G16H 40/20 |
| 2020/0331501 | A1 * | 10/2020 | Wirtz | G01C 21/3453 |
| 2020/0338303 | A1 * | 10/2020 | Engel | A47G 9/10 |

FOREIGN PATENT DOCUMENTS

| | | | | |
|---|---|---|---|---|
| DE | 102014222355 | A1 | | 5/2016 |
| DE | 102015122245 | A1 | | 6/2017 |
| DE | 102016221236 | A1 | | 5/2018 |
| DE | 102016224205 | A1 | | 6/2018 |
| DE | 102018111266 | A1 | | 11/2018 |
| DE | 102017212111 | A1 | | 1/2019 |
| DE | 102019002265 | A1 | | 9/2019 |
| KR | 20160148394 | A * | 12/2016 | ............ A61M 21/00 |
| KR | 20170057038 | A * | 5/2017 | ............ G06Q 30/02 |
| WO | WO-2012047977 | A2 * | 4/2012 | ............ G06Q 30/02 |
| WO | 2017102614 | A1 | | 6/2017 |

* cited by examiner

METHOD AND DEVICE FOR ADAPTING A DRIVING STRATEGY OF AN AT LEAST PARTIALLY AUTOMATED TRANSPORTATION VEHICLE

PRIORITY CLAIM

This patent application claims priority to German Patent Application No. 10 2019 204 201.5, filed 27 Mar. 2019, the disclosure of which is incorporated herein by reference in its entirety.

SUMMARY

Illustrative embodiments relate to a method and an apparatus for adapting a driving strategy of a transportation vehicle driving in at least semi-automated state.

BRIEF DESCRIPTION OF THE DRAWINGS

Disclosed embodiments are explained in more detail below with reference to the figures, in which.

DETAILED DESCRIPTION

Figure 1:
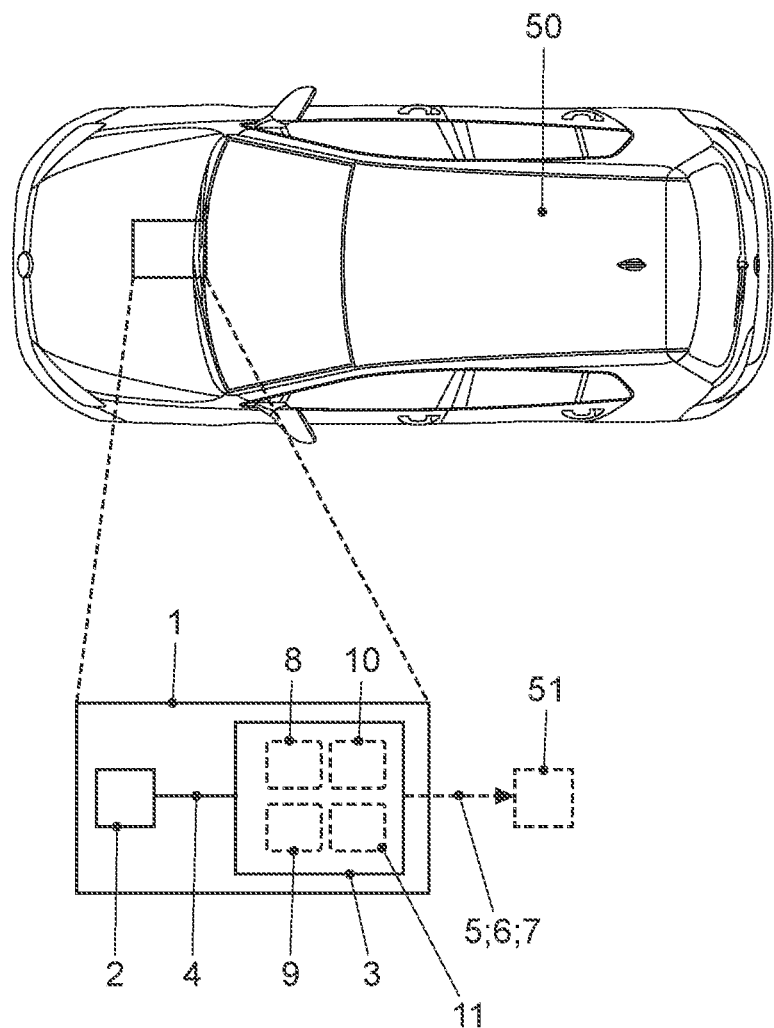
FIG. 1 shows a schematic depiction of an exemplary embodiment of the apparatus for adapting a driving strategy of a transportation vehicle driving in at least semi-automated state.

In future transportation vehicles driving in automated and semi-automated state, use scenarios become possible in which transportation vehicle occupants are able to relax or even fall asleep as they like. Of particular interest in this context are use scenarios in which people are taken from a starting location (e.g., front door) to a destination by a transportation vehicle driven in automated state, e.g., overnight, and the person is able to fall asleep during the journey.

DE 10 2016 221 236 A1 discloses a method for adapting the driving strategy of a transportation vehicle driving in at least semi-automated state, wherein the adapting takes place on the basis of an occupant condition and/or a condition of the current route or the route to be taken and/or a prescribed time of arrival at a destination or a combination of these.

DE 10 2015 122 245 A1 discloses a method for operating a transportation vehicle that involves a degree of tiredness of the driver of the transportation vehicle being determined by a condition monitoring device, wherein a transportation vehicle component of the transportation vehicle can be operated in a normal mode and in a rest mode, which is different than the latter, on the basis of the degree of tiredness, and a parameter characterizing the function of the transportation vehicle component is changed in the rest mode in regard to the awareness of the function that the driver feels.

DE 10 2013 012 750 A1 discloses a method for operating a driver assistance system that is designed for automatic driving by action in the engine controller, in a gearbox and in a braking system of a transportation vehicle, wherein a driver activates a sleep mode in which at least one transportation vehicle component is controlled such that it allows a comfortable period of rest or sleep for the driver.

DE 10 2014 222 355 A1 discloses smart glasses comprising a display and a sensor for measuring a property of the body of the wearer of the smart glasses, wherein at least one part of the sensor is configured to be in contact with the body of the wearer of the smart glasses when the smart glasses are worn as intended. The sensor can be used to determine, for example, a pulse, a skin conductance, a breathing rate, a breathing depth, a blood pressure, an oxygen saturation of the blood, an eyelid closure, a pupil size, tension variations on the surface of the head and/or a muscle contraction.

Disclosed embodiments provide an improved method and an improved apparatus for adapting a driving strategy of a transportation vehicle driving in at least semi-automated state that provide improved stimulation of restful sleep in an occupant.

This is achieved by a method and an apparatus.

A method for adapting a driving strategy of a transportation vehicle driving in at least semi-automated state is provided, wherein the adapting takes place on the basis of at least one occupant condition, captured by at least one sensor system, of an occupant, wherein a sleep phase is determined by the at least one sensor system during a sleeping condition of the occupant, and wherein the driving strategy is adapted by a control device on the basis of the determined sleep phase.

Further, an apparatus for adapting a driving strategy of a transportation vehicle driving in at least semi-automated state is provided, comprising at least one sensor system for capturing an occupant condition of an occupant, and a control device for adapting the driving strategy, wherein the at least one sensor system is designed to determine a sleep phase during a sleeping condition of the occupant, and wherein the control device is designed to adapt a driving strategy on the basis of the determined sleep phase.

In the disclosed embodiments, sleep by the occupant can be supported on the basis of a sleep phase that the occupant is currently in, which can increase a level of comfort, a level of fitness, a level of health and a level of wellbeing for the occupant.

It is assumed for the method described that the occupant under consideration is falling asleep, has already fallen asleep or is waking in the transportation vehicle driven in automated state. That is to say that the occupant is in one of multiple sleep phases.

Healthy sleep has multiple associated sleep phases. Usually, a distinction is drawn between four or five of such sleep phases (e.g., awake, REM, I, II, III, IV). The sleep phases (also referred to as sleep stages) are best recognized from a brain activity, which can be determined by an electroencephalogram (EEG), for example. From falling asleep to deep sleep, sleep remains substantially uniform. This changes abruptly with the onset of what is known as REM sleep or dream sleep. The REM phase owes its name to the rapid eye movement characteristic of this period of sleep. REM stands for "rapid eye movement". Brain activity speeds up considerably and the EEG shows many small deflections—similarly to falling asleep. Particularly in the REM sleep phase, human beings dream. Sleep researchers assume that emotional sensory impressions above all, but also information, are processed in the REM sleep phase.

The falling-asleep phase is also referred to as sleep phase 1. As the name suggests, it involves the first few minutes while falling asleep and thereafter. The falling-asleep phase is above all characterized in that the organism descends ever further into calm and relaxation. The pulse slows, breathing becomes deeper and the number of breaths decreases. Many people experience the falling-asleep phase as a time of becoming heavy or falling, which is perceived in a dream-like way. In the falling-asleep phase, sleep is still very superficial. Just small disturbances can wake the sleeping person—after waking, he is immediately wide awake again.

The light sleep phase makes up about half of sleep. It is also referred to as sleep phase 2. Sometimes, sleep phases 1 and 2 are also grouped into the light sleep phase: in this phase, brain activity is restricted to low frequencies above all. Consciousness is shut down, and the person sleeps with relaxed muscles and almost no eye movement.

In the deep sleep phase, human beings recover particularly well. As the name states, a person sleeps deeply and soundly in this sleep phase. Many people can be woken only with very great difficulty in the deep sleep phase. If this happens, a person regains consciousness only slowly. The deep sleep phase is also the sleep phase with the deepest physical relaxation. Many investigations verify that the deep sleep phase is the most valuable sleep phase for physical and mental recovery. Sleep researchers also divide the deep sleep phase into sleep phases 3 and 4.

In healthy people, the sequence of the sleep phases is repeated several times per night with good sleep. One complete cycle lasts approximately 90 minutes—plus or minus 10 minutes. Of these, approximately 50 minutes account for falling-asleep and light sleep phases. The deep sleep phase and the REM sleep phase make up approximately 40 minutes of this sleep cycle. At the start of the night, deep sleep dominates, and toward the end of the sleeping time the body stays increasingly in the REM sleep phases and prepares for waking.

As already described, the sleep phases can be determined from a brain activity. Depending on the frequency of brainwaves captured at the scalp of a human being by electroencephalogram (EEG) sensors, a distinction is made between beta waves (12-30 Hz), alpha waves (8-12 Hz), theta waves (4-7 Hz) and delta waves (0-4 Hz). Alpha waves occur during relaxation with eyes closed. A transition from alpha waves to theta waves occurs during light sleep shortly after falling asleep (sleep stage I). In sleep stage II, theta waves continue to occur. In sleep stage III, which marks a transition to the deep sleep phase, delta waves increasingly occur. Sleep stage IV, in which the body is in deep sleep, corresponds substantially to a high proportion of delta waves. REM sleep is similar to sleep stage I, that is to say that predominantly theta waves occur, and there is additionally the eye movement already described.

The sensor system is used to determine such a sleep phase in the occupant during a sleeping condition. In this instance, the sleeping condition denotes a condition opposite to a waking condition, although a boundary between a waking condition and a sleeping condition does not have to be keenly developed. The sensor system in this case can comprise various sensors, e.g., camera-based motion detection, sensors for capturing brainwave activity, electroencephalogram (EEG) sensors, motion sensors, for example, as an armband, sensors for capturing a breathing rate, a heart rate and/or a body and/or skin temperature and/or other vital functions of the body. The vital functions captured by the sensors can be used at least to assess a current sleep phase. By way of example, motion patterns provide information about how deeply the body is sleeping. A body temperature and a breathing rate also provide indications of how deeply the body is sleeping. Further, a brain activity can also be determined from a state of excitement or a level of tension in neck muscles, for example, since this correlates with brain activity. When virtual reality or augmented reality glasses are used, there can be provision for skin contact sensors arranged on the glasses to be used to capture a brain activity and to determine a sleep phase therefrom, for example.

When the sleep phase has been determined, the driving strategy is adapted by the control device on the basis of the determined sleep phase. To this end, the control device can accordingly communicate with a transportation vehicle controller, for example, via a bus system of the transportation vehicle, and transmit appropriate instructions for adapting the driving strategy to the transportation vehicle controller. In this instance, the driving strategy comprises both a journey route, that is to say a set of driving maneuvers, and a driving style, that is to say the manner in which the transportation vehicle covers a journey route or individual driving maneuvers and how (dynamically) the transportation vehicle is controlled in automated state.

The control device and the sensor system can each be a combination of hardware and software, for example, as program code executed on a microcontroller or microprocessor.

There can be provision for at least one journey route and/or a driving style to be adapted and/or selected on the basis of the determined sleep phase to adapt the driving strategy. A journey route in this instance is supposed to denote a trajectory of the transportation vehicle, that is to say a set of interlinked positions in a coordinate system, for example, on the basis of positions on roads on a road map. A driving style is supposed to denote the manner in which such a trajectory, that is to say the individual interlinked positions, is covered. The driving style comprises limit values for a longitudinal and a transverse acceleration and also for velocities.

In at least one disclosed embodiment, there can be provision in this instance for the journey route to be selected or adapted such that a sleep by the occupant is stimulated on the basis of the determined sleep phase or in a manner geared thereto. Depending on the currently existing sleep phase that the occupant is in, the occupant is more or less sensitive toward external environmental influences. This can be taken into consideration when adapting the driving strategy, in particular, when selecting or adapting the journey route and/or the driving style.

In at least one disclosed embodiment, there is provision for a sensitivity value for the sleeping occupant in respect of external environmental influences to be estimated or stipulated by the control device on the basis of the determined sleep phase, wherein the driving strategy is adapted on the basis of the estimated or stipulated sensitivity value. A possible driving strategy and, in particular, a possible journey route or a possible driving style can then be assigned an influence value, or such an influence value can be assessed for the respective journey route. All of the properties of the journey route can be taken into consideration in this instance, for example, a route (curve sections, straight sections, tunnels, urban traffic, freeways, rural roads, etc.), required accelerations and decelerations, etc. The influence value of a journey route can then be compared with the assessed or stipulated sensitivity value and a journey route can be selected or adapted on the basis of a comparison result. In the simplest case, the sensitivity value and the influence value have the same dimension, which means that they can be compared with one another directly. The sensitivity value can then serve as a threshold value, downward or upward transgression of which determines the selection or adaptation of the journey route. There can also be provision for different dimensions, however, so that a comparison or the selection and adaptation is made by appropriate conversions or calculations.

There can be provision, by way of example, for the transportation vehicle to be moved exclusively during a deep sleep phase, because the human body is largely insensitive toward external environmental influences in this phase. By contrast, there can be provision for the transportation vehicle to be moved as little as possible or not at all while an occupant is falling asleep and in the light sleep phase.

In a disclosed embodiment, there is provision for the driving strategy to be adapted on the basis of an assessed or expectable loudness on a journey route implemented as part of the driving strategy. To this end, for example, an average loudness value or a noise level can be determined and/or assessed and, on the basis of the estimated or stipulated sensitivity value, used to select a journey route on the basis of the determined sleep phase. By way of example, in the lighter sleep phases, journey routes can be selected for which a low average loudness value has been estimated. In a deep sleep phase, on the other hand, journey routes can be selected independently of an average loudness. Alternatively or additionally, a maximum loudness value can also be assessed and used to select or adapt the journey route. The loudness can be assessed either by a simulation or on the basis of empirical measurements. By way of example, a road type (minor road, main road, federal road, freeway, etc.) may have been taken as a basis for storing in a road map how loud respective route sections are or how high a respective expectable noise level is. On the basis of these loudness estimates or noise level estimates stored in the road map and a planned journey route, a total noise level that results for the sleeping occupant can be estimated. The loudness can further be alternatively or additionally assessed on the basis of current traffic reports, for example, on the basis of a current traffic density. Weather information can also be taken into consideration, for example, to avoid noise pollution from rain and/or bad weather by adapting the journey route.

In at least one disclosed embodiment, there is provision for the driving strategy to be adapted by decreasing accelerations if a sleep phase with a shallow depth of sleep has been determined and increasing accelerations if a deep sleep phase has been determined as sleep phase. This has the benefit that mechanical environmental influences on the sleeping occupant are minimized in the light sleep phases, whereas the occupant is transported unhindered in the deep sleep phase, which is less sensitive toward environmental influences. Further, this also allows a loudness or noise level to be adjusted.

In a further disclosed embodiment, there is provision for the transportation vehicle to be brought to a standstill if a falling-asleep phase has been determined as sleep phase, wherein, to this end, a suitable journey route is chosen or the journey route is adapted accordingly. This has the benefit that the (falling-asleep) sleeping occupant is helped to fall asleep, because the fact that the transportation vehicle is at a complete standstill leads to minimization of environmental influences, in particular, mechanical environmental influences such as accelerations. A loudness is also normally minimized as a result of the transportation vehicle being at a complete standstill. There can be provision for the suitable journey route to be selected such that it is possible to drive to a quiet location to come to a standstill in as short a time as possible after the occupant falls asleep. Further, there can be provision for safety criteria (protection from robberies, etc.) also to be taken into consideration when choosing the location to come to a standstill.

In at least one disclosed embodiment, there is provision for a future sleep phase and/or a waking time or waking time window for the sleeping occupant to be estimated on the basis of a determined sleep phase and/or an ascertained time characteristic of determined sleep phases. This can be effected on the basis of a sleep cycle. On the basis of the determined current sleep phase and/or the ascertained time characteristic of the determined sleep phases, a time or a time window for the entry of the sleeping occupant into another sleep phase can then be assessed on the basis of the sleep cycle. This can be used to select or adapt a journey route predictively. If, for example, the transportation vehicle is at a standstill because the occupant is currently in a lighter sleep phase, a time or a time window for a transition to a deep sleep phase can be estimated and a journey route can be predictively chosen or adapted that already slowly navigates the transportation vehicle from a parking space onto a rural road.

In at least one disclosed embodiment, there is provision for at least one infrastructure property to be selected on the basis of the determined sleep phase and/or an estimated future sleep phase, wherein a journey route is additionally chosen or adapted on the basis of the at least one infrastructure property of the journey route. An infrastructure property can be, for example, a rest area having a public toilet on a freeway or a rural road. A service area, for example, with a restaurant or a café, can also be such an infrastructure property. Further, a conventional or electric filling station can also be such an infrastructure property. As such, on the basis of an expected light sleep phase and subsequent waking of the sleeping occupant, for example, a service area with a toilet can be driven to allow the occupant to use the toilet and freshen up and, further, to access food and beverages for refreshment. If the transportation vehicle is at a standstill to allow the occupant to sleep restfully in lighter sleep phases, a charging station at an electric filling station can be driven to, so that an electric transportation vehicle can be charged in the period of the standstill. The journey route can be predictively selected or predictively adapted on the basis of the determined current sleep phase and, in particular, on the basis of an estimated future sleep phase while taking into consideration the desired infrastructure property.

In a disclosed embodiment, there is provision for a sleeping occupant to be woken on the basis of the estimated waking time or waking time window. As a result of waking at the estimated waking time or in an estimated waking window, the sleeping occupant finds waking particularly pleasant.

In at least one disclosed embodiment, there is provision for at least one sleep profile of an occupant to be stored or to be able to be stored in the control device, wherein the driving strategy is adapted on the basis of the stored sleep profile of the occupant. To this end, the control device comprises a memory device, for example, in which the at least one sleep profile is stored. Further, there can also be provision for the occupant to store the sleep profile in the control device or the memory device when getting into the transportation vehicle. The sleep profile comprises preferences in respect of a behavior of the transportation vehicle for the individual sleep phases of the occupant. As such, an occupant who is generally less sensitive can, for example, also determine that the transportation vehicle can use any journey routes or journey routes having specific properties in lighter sleep phases. By contrast, an occupant with sensitive sleep can use the sleep profile to prescribe that the transportation vehicle is brought to a standstill in the lighter sleep phases and can be moved exclusively in the deep sleep phases. Further, limit values for maximum accelerations that can occur on a journey can also be prescribed in the sleep profile. Further, usual falling-asleep times for the occupant can also be stored in the sleep profile, which allows predictive planning of journey routes. This allows a level of comfort and a rest to be stipulated and increased on an occupant-individual basis.

If there are multiple occupants in the transportation vehicle, then, for example, an appropriate set of rules can be used to prescribe which of the occupants is given preference. By way of example, it may be prescribed that the journey route is adapted only if all occupants are asleep. Alternatively, it may be prescribed that a compromise is found between occupants who are asleep and occupants who are awake in respect of a journey route and/or a driving style. By way of example, a driving style can be adapted if at least one of multiple occupants is asleep, but the transportation vehicle is not brought to a standstill, so as not to delay an onward journey for the occupants who are not asleep.

To stimulate sleep by the occupant or occupants, there can be provision for a transportation vehicle interior to be darkened in a sleeping condition, that is to say largely independently of the specifically determined sleep phase.

There can further be provision to use machine learning methods to find out for an occupant which driving strategy promotes restful sleep and which driving strategies are a hindrance. Properties of the driving strategies for restful sleep can then be stored in the control device in a sleep profile, for example.

Features to refine the apparatus emerge from the description of refinements of the method. The benefits of the individual refinements of the apparatus are the same in this case as in the case of the refinements of the method.

FIG. 1 shows a schematic depiction of an exemplary embodiment of the apparatus 1 for adapting a driving strategy 5 of a transportation vehicle 50 driving in at least semi-automated state. The transportation vehicle 50 can be driven in automated state, so that an occupant of the transportation vehicle 50 does not need to manually control the transportation vehicle 50 during the journey and can sleep. The apparatus 1 comprises a sensor system 2 for capturing a sleeping condition of an occupant of the transportation vehicle 50 and a control device 3. The sensor system 2 and control device 3 can be a combination of hardware and software, for example, as program code executed on a microcontroller or microprocessor.

The sensor system 2 in this case can comprise various sensors, e.g., camera-based motion detection, sensors for capturing brainwave activity, electroencephalogram (EEG) sensors, motion sensors, for example, as an armband, sensors for capturing a breathing rate, a heart rate and/or a body temperature and/or other vital functions. When virtual reality or augmented reality glasses are used, there can be provision, by way of example, for skin contact sensors arranged on the glasses to be used to capture a brain activity and to determine a sleep phase therefrom. The vital functions captured by the sensors can be used at least to assess a current sleep phase. By way of example, motion patterns provide information about how deeply the body is sleeping. A body temperature and a breathing rate also provide indications of how deeply the body is sleeping. Further, a brain activity can also be determined from a state of excitement or a level of tension in neck muscles, for example, since this correlates with brain activity. A sensor for capturing a state of excitement or a tension in neck muscles can be arranged in a headrest of a seat of the transportation vehicle 50, for example.

The sensor system 2 determines a sleep phase 4 during a sleeping condition of an occupant of the transportation vehicle 50. This is done by virtue of, for example, brainwaves of the occupant being captured by the sensor system 2 and the brainwaves being classified on the basis of frequency (e.g., into alpha, beta, theta, delta waves). From the associated class, the currently existing sleeping condition 4 of the occupant is determined and transferred to the control device 3. By way of example, the sleep phase 4 may be one of the following: falling-asleep phase, light sleep phase, deep sleep phase, REM sleep phase.

On the basis of the determined sleep phase 4, the control device 3 adapts a driving strategy 5. The driving strategy 5 can comprise both a journey route 6 and a driving style 7. The driving strategy 5 is adapted by the control device 3 in this case such that sleep and recovery by the sleeping occupant are promoted. The driving strategy 5 and a journey route 6 and/or a driving style 7 are supplied by the control device 3 to a transportation vehicle controller 51, which implements the driving strategy 5 accordingly.

In this instance, there can be provision for a sensitivity value 8 for the sleeping occupant toward external environmental influences to be estimated or stipulated by the control device 3 on the basis of the determined sleep phase 4, wherein the driving strategy 5 is adapted on the basis of the estimated or stipulated sensitivity value 8. A possible driving strategy 5 and, in particular, a possible journey route 6 or a possible driving style 7 can each be assigned an influence value, or such an influence value can be assessed for the respective driving strategy 5, etc. This can involve all of the properties of the journey route 6 being taken into consideration, for example, a route (curve sections, straight sections, tunnels, urban traffic, freeways, urban roads, etc.), necessary accelerations and decelerations, etc. The influence value of a driving strategy 5 can then be compared with the assessed or stipulated sensitivity value 8, and a driving strategy 5 or a journey route 6 and/or a driving style 7 can be selected or adapted on the basis of a comparison result.

There can be provision for the driving strategy 5 to be adapted on the basis of an assessed or expectable loudness on a journey route 6 implemented as part of the driving strategy 5.

There can further be provision for the driving strategy 5 to be adapted by decreasing accelerations when a sleep phase 4 with a shallow depth of sleep (light sleep phase) has been determined and increasing accelerations when a deep sleep phase has been determined as sleep phase 4.

Further, there can be provision for the transportation vehicle 50 to be brought to a standstill if a falling-asleep phase has been determined as sleep phase 4, wherein, to this end, a suitable journey route 6 is chosen or the journey route 6 is adapted accordingly.

There can be provision for a future sleep phase 9 and/or a waking time 10 for the sleeping occupant to be estimated on the basis of a determined sleep phase 4 and/or an ascertained time characteristic of determined sleep phases 4.

Further, there can be provision for at least one infrastructure property to be selected on the basis of the determined sleep phase 4 and/or an estimated future sleep phase 9, wherein a journey route 6 is additionally chosen or adapted on the basis of the at least one infrastructure property of the journey route 6.

As a development, there can be provision for a sleeping occupant to be woken on the basis of the estimated waking time 10.

There can be provision for at least one sleep profile 11 of an occupant to be stored or to be able to be stored in the control device 3, wherein the driving strategy 5 is adapted on the basis of the stored sleep profile 11 of the occupant.

Figure 2:
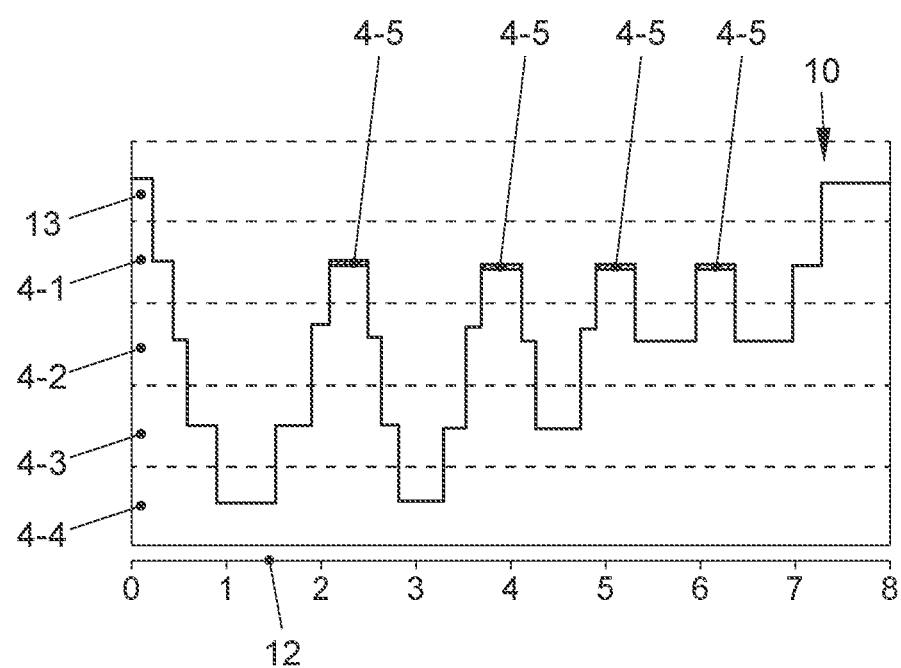
FIG. 2 shows a schematic depiction of individual sleep phases of a typical night-time sleep by a human being.

FIG. 2 shows a schematic depiction of individual sleep phases 4-x of a typical night-time sleep of a human being on the basis of a period 12 after falling asleep to clarify the disclosure. After falling asleep, the body needs about 1 hour to get from an awake condition 13 through the sleep phases 4-1, 4-2, 4-3 to a sleep phase 4-4 of deep sleep. After about another 90 minutes, the body is in the sleep phase 4-1 again, that is to say in a light sleep phase, with REM sleep 4-5 occurring in this sleep phase 4-1. Subsequently, the sleep becomes deeper again and there follows a further sleep phase 4-4 of deep sleep. After about half the night, that is to say after approximately 4 hours, no further deep sleep takes place and the body remains in the lighter sleep phases 4-1, 4-2, 4-3, with sleep becoming ever lighter and then only being in the sleep phases 4-1, 4-2 in the last few hours of the night.

Depending on the sleep phase 4-1, 4-2, 4-3, 4-4, 4-5, the body is more sensitive to external environmental influences, such as, for example, mechanical influences, such as jolts and/or accelerations, light and/or noise. This is taken into consideration for adapting the driving strategy by virtue of the transportation vehicle being moved to a lesser extent or not at all (standstill) in the lighter sleep phases 4-1, 4-2, for example, in which the body is more sensitive. In the deeper sleep phases 4-3, 4-4, in particular, during deep sleep in the sleep phase 4-4, the transportation vehicle can be moved without limitation, on the other hand, which means that no or only few limitations need to be performed when selecting a journey route or a driving style.

There can further be provision for the driving strategy, in particular, a journey route, to be adapted such that an infrastructure can be provided, such as, for example, a toilet and/or a rest area, etc., during the lighter sleep phases 4-1, 4-2 or in expectation of the lighter sleep phases 4-1, 4-2. To this end, a rest area is driven to during these sleep phases 4-1, 4-2, for example.

Figure 3:
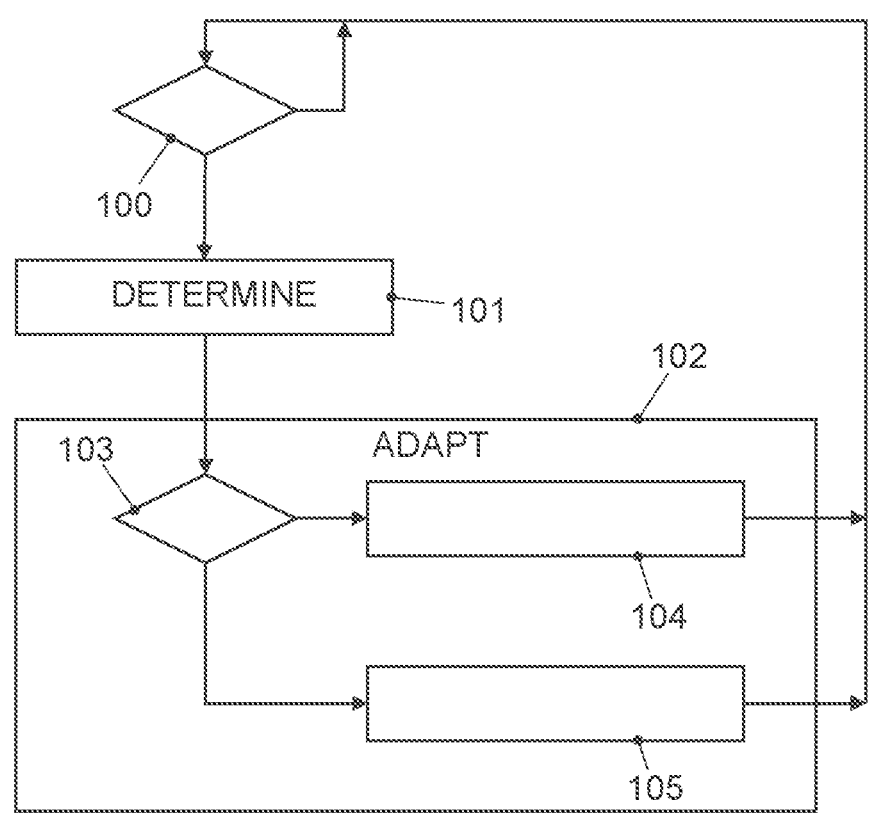
FIG. 3 shows a schematic flowchart for the method for adapting a driving strategy of a transportation vehicle driving in at least semi-automated state.

FIG. 3 shows a schematic flowchart for the method for adapting a driving strategy of a transportation vehicle driving in at least semi-automated state.

The method is started when a sleeping condition of an occupant of the transportation vehicle is captured and determined. To this end, a method operation at 100 involves a check being performed to determine whether or not the occupant is sleeping. This is done using a sensor system. If the occupant is sleeping, the method is started in method operation at 101. If the occupant is not sleeping, the method returns to step 100 to continue performing the check on the occupant.

In method operation at 101, a sleep phase is determined by at least one sensor system during the sleeping condition of the occupant. This is done, for example, on the basis of brainwave analyses and/or an evaluation of a state of excitement of neck muscles of the occupant. Motion patterns of the occupant can also be captured and evaluated, as can a heartbeat, a breathing rate, eye movement and/or other vital functions.

In method operation at 102, the driving strategy is adapted by a control device on the basis of the determined sleep phase. In this instance, adapting also means that a driving strategy can be maintained if it is suitable or if a sleep phase does not change. In this regard, method operation at 102 comprises method operations at 103-105.

Two possible scenarios during the sleep of an occupant of the transportation vehicle are assumed below to simplify matters. In this case, a distinction will merely be drawn between a light sleep phase and a deep sleep phase.

In a method operation at 103, a check is performed to determine whether the current sleep phase determined in method operation at 101 is a light sleep phase. If this is the case, method operation at 104 involves a driving strategy of the transportation vehicle driving in automated state being adapted or set. The driving strategy comprises both the journey route and a driving style in this instance. By way of example, there can be provision for the transportation vehicle to be driven to the next parking space, so that the light sleep phase of the occupant is not disturbed or sleep is stimulated. The adapted driving strategy is transferred to a transportation vehicle controller, for example, by the control device for implementation.

If, on the other hand, the result of the check in method operation at 103 is that there is no light sleep phase, but rather a deep sleep phase, then method operation at 105 involves the driving strategy being adapted such that transport to a destination is performed as rapidly as possible. To this end, a journey route and a driving style are adapted; in particular, fast roads can be preferred and more powerful accelerations can be employed. The adapted driving strategy is transferred to a transportation vehicle controller, for example, by the control device for implementation.

Subsequently, the method is repeated by returning to method operation at 100.

In method operations at 104 and 105, there can be provision for a sensitivity value of the sleeping occupant toward external environmental influences to be estimated or stipulated by the control device on the basis of the determined sleep phase, wherein the driving strategy is adapted on the basis of the estimated or stipulated sensitivity value.

Further, as a development, there can be provision for the driving strategy to be adapted on the basis of an assessed or expectable loudness on a journey route implemented as part of the driving strategy.

LIST OF REFERENCE SIGNS

1 Apparatus
2 Sensor system
3 Control device
4 Sleep phase
4-x Sleep phase
4-5 REM sleep phase
5 Driving strategy
6 Journey route
7 Driving style
8 Sensitivity value
9 Future sleep phase
10 Waking time
11 Sleep profile
12 Period
13 Awake condition
20 Period
50 Transportation vehicle
51 Transportation vehicle controller
100-105 Method operations

The invention claimed is:

1. An apparatus for adapting a driving strategy of a transportation vehicle driving in at least a semi-automated state, the apparatus comprising:
   at least one sensor system for capturing an occupant condition of an occupant; and
   a control device for adapting the driving strategy,
   wherein the at least one sensor system determines a sleep phase during a sleeping condition of the occupant, and wherein the control device adapts the driving strategy based on the determined sleep phase, wherein responsive to determination of a falling-asleep phase in which the occupant is superficially sleeping while initially falling asleep as the determined sleep phase, the transportation vehicle is brought to a standstill to assist the occupant in falling asleep, wherein a suitable journey route is chosen or the journey route is adapted accordingly.

2. The apparatus of claim 1, wherein a sensitivity value for the occupant in the sleeping condition in respect of external environmental influences is estimated or stipulated by the control device based on the determined sleep phase, wherein the driving strategy is adapted based on the estimated or stipulated sensitivity value.

3. The apparatus of claim 2, wherein the driving strategy is adapted based on an assessed or expectable loudness on a journey route implemented as part of the driving strategy.

4. The apparatus of claim 1, wherein the driving strategy is adapted by decreasing accelerations in response to the sleep phase with a shallow depth of sleep being determined and increasing accelerations in response to a deep sleep phase being determined.

5. The apparatus of claim 1, wherein a future sleep phase and/or a waking time or waking time window for the occupant in the sleeping condition is estimated based on the determined sleep phase and/or an ascertained time characteristic of determined sleep phases.

6. The apparatus of claim 5, wherein the occupant in the sleeping condition is woken based on the estimated waking time or waking time window.

7. The apparatus of claim 1, wherein at least one infrastructure property is selected based on the determined sleep phase and/or an estimated future sleep phase, wherein a journey route is additionally chosen or adapted based on at least one infrastructure property of the journey route.

8. The apparatus of claim 1, wherein at least one sleep profile of the occupant is stored in the control device, wherein the driving strategy is adapted based on the stored sleep profile of the occupant.

9. A method for adapting a driving strategy of a transportation vehicle driving in at least a semi-automated state, wherein the adapting takes place based on at least one occupant condition, captured by at least one sensor system, of an occupant, the method comprising:
determining a sleep phase by the at least one sensor system during a sleeping condition of the occupant; and
adapting the driving strategy by a control device based on the determined sleep phase, including, responsive to determination of a falling-asleep phase in which the occupant is superficially sleeping while initially falling asleep as the determined sleep phase, bringing the transportation vehicle to a standstill to assist the occupant to fall asleep, wherein a suitable journey route is chosen or the journey route is adapted accordingly.

10. The method of claim 9, wherein a sensitivity value for the occupant in the sleeping condition in respect of external environmental influences is estimated or stipulated by the control device based on the determined sleep phase, wherein the driving strategy is adapted based on the estimated or stipulated sensitivity value.

11. The method of claim 10, wherein the driving strategy is adapted based on an assessed or expectable loudness on a journey route implemented as part of the driving strategy.

12. The method of claim 9, wherein the driving strategy is adapted by decreasing accelerations in response to the sleep phase with a shallow depth of sleep being determined and increasing accelerations in response to a deep sleep phase being determined.

13. The method of claim 9, wherein a future sleep phase and/or a waking time or waking time window for the occupant in the sleeping condition is estimated based on the determined sleep phase and/or an ascertained time characteristic of determined sleep phases.

14. The method of claim 13, wherein the occupant in the sleeping condition is woken based on the estimated waking time or waking time window.

15. The method of claim 9, wherein at least one infrastructure property is selected based on the determined sleep phase and/or an estimated future sleep phase, wherein a journey route is additionally chosen or adapted based on at least one infrastructure property of the journey route.

16. The method of claim 9, wherein at least one sleep profile of the occupant is stored in the control device, wherein the driving strategy is adapted based on the stored sleep profile of the occupant.

17. A transportation vehicle for adapting a driving strategy in at least a semi-automated state, the transportation vehicle comprising:
at least one sensor system for capturing an occupant condition of an occupant; and
a control device for adapting the driving strategy,
wherein the at least one sensor system determines a sleep phase during a sleeping condition of the occupant, and
wherein the control device adapts the driving strategy based on the determined sleep phase, wherein responsive to determination of a falling-asleep phase in which the occupant is superficially sleeping while initially falling asleep as the determined sleep phase, the transportation vehicle is brought to a standstill to assist the occupant in falling asleep, wherein a suitable journey route is chosen or the journey route is adapted accordingly.

* * * * *